US011219703B2

(12) United States Patent
Béduer et al.

(10) Patent No.: US 11,219,703 B2
(45) Date of Patent: Jan. 11, 2022

(54) SHAPEABLE SCAFFOLD MATERIAL AND USES THEREOF

(71) Applicant: École Polytechnique Fédérale de Lausanne (EPFL), Lausanne (CH)

(72) Inventors: Amélie Barbara Hildegarde Béduer, Lausanne (CH); Thomas Braschler, Chavannes-Renens (CH); Philippe Renaud, Préverenges (CH); Giorgio Pietramaggiori, Lausanne (CH); Saja Scherer, Lausanne (CH)

(73) Assignee: École Polytechnique Fédérale de Lausanne (EPFL), Lausanne (CH)

( * ) Notice: Subject to any disclaimer, the term of this patent is extended or adjusted under 35 U.S.C. 154(b) by 0 days.

(21) Appl. No.: 15/752,752

(22) PCT Filed: Aug. 18, 2016

(86) PCT No.: PCT/IB2016/054947
§ 371 (c)(1),
(2) Date: Feb. 14, 2018

(87) PCT Pub. No.: WO2017/029633
PCT Pub. Date: Feb. 23, 2017

(65) Prior Publication Data
US 2018/0250444 A1 Sep. 6, 2018

(51) Int. Cl.
*A61L 27/56* (2006.01)
*A61L 24/04* (2006.01)
*A61L 27/34* (2006.01)
*A61L 15/42* (2006.01)
*A61L 15/28* (2006.01)
*A61L 27/50* (2006.01)
*A61L 27/20* (2006.01)
*A61L 27/36* (2006.01)
*A61L 27/52* (2006.01)
*A61L 27/38* (2006.01)
*A61L 27/22* (2006.01)

(52) U.S. Cl.
CPC ............ *A61L 27/56* (2013.01); *A61L 27/227* (2013.01); *A61L 27/3616* (2013.01); *A61L 27/38* (2013.01); *A61L 27/50* (2013.01); *A61L 27/52* (2013.01); *A61L 27/505* (2013.01)

(58) Field of Classification Search
CPC ...... C08L 1/02; A61L 27/56; A61L 2300/412; A61L 27/52; A61L 27/18; A61L 27/58; A61L 2400/06; A61L 2430/00; A61L 2430/34; A61L 2430/02; A61L 26/0023; A61L 31/10; A61L 26/0061; A61L 27/34; A61L 15/28; A61L 27/50; A61L 15/425; A61L 27/20; A61L 24/0036
See application file for complete search history.

(56) References Cited

U.S. PATENT DOCUMENTS

| 5,632,774 | A | 5/1997 | Babian |
| 2005/0186240 | A1 | 8/2005 | Ringeisen et al. |
| 2009/0326654 | A1 | 12/2009 | Powell |
| 2011/0293722 | A1* | 12/2011 | Kaully ................. A61K 9/0007 424/488 |
| 2014/0308362 | A1* | 10/2014 | Bellas ..................... A61L 27/54 424/499 |

FOREIGN PATENT DOCUMENTS

WO   WO-2016011387 A1 *  1/2016 ......... A61L 26/0047

OTHER PUBLICATIONS

Shandalov, Yulia et al., "An engineered muscle flap for reconstruction of large soft issue defects," Proceeding of the National Academy of Sciences of the United States of America, Apr. 2014, pp. 6010-6015, vol. 111, No. 16, USA.
Findlay, Michael W. et al.,"Tissue-Engineered Breast Reconstruction: Bridging the Gap toward Large-Volume Tissue Engineering in Humans", Plastic and Reconstructive Surgery, Dec. 2011, pp. 1206-1215, vol. 128, No. 6, American Society of Plastic Surgeons, USA.
Coleman, Sydney R. et al., "Fat Grafting to the Breast Revisited: Safety and Efficacy", Plastic and Reconstructive Surgery, Mar. 2007, pp. 775-785, vol. 119 No. 3, American Society of Plastic Surgeons, USA.
Claro, F. et al., "Applicability and safety of autologous fat for reconstruction of the breast", British Journal of Surgery, Apr. 2012, pp. 768-780, vol. 99 No. 6, Wiley, United Kingdom.
Howes, Benjamin H.L. et al., "Autologous Fat Grafting for Whole Breast Reconstruction", Plastic Reconstruction Surgery Global Open, Mar. 2014, pp. e124, vol. 2 No. 3, National Center for Biotechnology Information, USA.
Mao, Jeremy J. et al., "Facial Reconstruction by Biosurgery: Cell Transplantation versus Cell Homing", Tissue Engineering Part B: Reviews, Mar. 2010, pp. 257-262, vol. 16 No. 2, Mary Ann Liebert Inc., USA.
Sterodimas, Aris et al., "Tissue engineering with adipose-derived stem cells (ADSCs): Current and future applications", Journal, Nov. 2010, pp. 1886-1892, vol. 63 No. 11, Elsevier, Great Britain.

(Continued)

*Primary Examiner* — Tracy Liu
(74) *Attorney, Agent, or Firm* — Pabst Patent Group LLP

(57) ABSTRACT

The invention relates to a scaffold material comprising a plurality of particles of a highly porous polymeric material, characterized in that said scaffold material becomes a shapeable paste once hydrated. The specific features of the particle material impart a special behavior to the scaffold, which can be easily shaped and even highly reversibly compressed, so that in certain aspects it can, if needed, be injected, said capacity to be shaped being maintained over a high range of hydration conditions. A particular aspect of the invention relates, therefore, to the use of such scaffold material for the manufacturing of shapeable body implants, such as breast implants, to the shapeable body implants themselves as well as to non-invasive methods for using thereof in creating or reconstructing a three-dimensional volume in a subject's body part.

22 Claims, 5 Drawing Sheets

(56) References Cited

OTHER PUBLICATIONS

Pereira, Luis Haroldo et al., "Long-term fate of transplanted autologous fat in the face", Journal of Plastic, Reconstructive & Aesthetic Surgery, Jan. 2010, pp. e68-e69, vol. 63 No. 1, Elsevier, Great Britain.

Maiti, et al., "In vivo measurement of skin surface strain and sub-surface layer deformation induced by natural tissue stretching", J. of the Mech. Behavior of Biomed. Mater., 62:556-569 (2016).

* cited by examiner

A

B

SHAPEABLE SCAFFOLD MATERIAL AND USES THEREOF

CROSS-REFERENCE TO RELATED APPLICATIONS

The present application claims the priority of British application GB 1514788.7 that was filed on Aug. 20, 2015, the entire contents thereof being herewith incorporated by reference.

FIELD OF INVENTION

The present invention pertains the field of scaffold materials that may be advantageously used as biomaterials for tissue repair.

BACKGROUND ART

Successful restoration of substantial large soft tissue defects, caused by severe trauma or cancer ablation, poses a significant clinical challenge (Shandalov, Y. et al. Proc. Natl. Acad. Sci. U.S.A. 111, 6010-6015 (2014)). The current therapeutic approach involves grafts, for example with lipoaspirate material from the patient, synthetic material replacement (prosthetic implants), and autologous tissue transfer by means of tissue flaps.

Numerous works report successful generation of tissue for repair of a variety of tissue defects, such as breast reconstruction with adipose tissue (also called lipofilling) (Findlay, M. W. et al. Plast. Reconstr. Surg. 128, 1206-1215 (2011)) and various aesthetic restorations in the face and the body (Mao, J. J. et al., Tissue Eng. Part B Rev. 16, 257-262 (2010); Sterodimas, A. et al., J. Plast. Reconstr. Aesthetic Surg. JPRAS 63, 1886-1892 (2010); Pereira, L. H. & Sterodimas, A. J. Plast. Reconstr. Aesthetic Surg. JPRAS 63, e68-69 (2010)). The use of autologous tissue is ideal; however, insufficient donor tissue limit its use. Now with increasing reports of success (Coleman, S. R. & Saboeiro, A. P. Plast. Reconstr. Surg. 119, 775-785; discussion 786-787 (2007); Claro, F. et al., Br. J. Surg. 99, 768-780 (2012); Howes, B. H. L. et al. Plast. Reconstr. Surg. Glob. Open 2, (2014)) surgeons are trying to establish techniques to provide the best results with fat grafting. A major problem remains however the loss of volume few weeks or months after the reconstructive surgery which adversely affects patient satisfaction and requires further reconstructive procedures. Previous studies that report graft loss vary greatly in technique, amount lost, and methods in which loss was measured; the outcome of the reconstructive surgery being not predictable.

SUMMARY OF INVENTION

Bearing in mind all the drawbacks of the prior art approaches, and in order to tackle and overcome them, the present inventors developed a new scaffold material, as defined in the claims, that consists of a paste that can be shaped and modelled (hereafter referred to as "shapeable" or "malleable" paste), as well as an associated device and method for using thereof, particularly but not exclusively intended for three-dimensional tissue volume reconstruction in plastic/reconstructive surgery. In the present invention, a material is considered shapeable if it can be deformed to arbitrary shapes by applying a force higher than a given threshold force, the achieved shapes then remaining stable against forces smaller than the threshold. In other words, the shapeable material behaves approximately like a viscous liquid for forces larger than the threshold force and as an elastic solid for forces below the threshold force.

By contacting small particles of a material having a high porosity and high reversible compressibility properties with a sufficient amount of a liquid (e.g. water), it is possible to obtain a "scaffold paste" that is shapeable.

One of the key features of the scaffold material of the invention is that it substantially consists of partially or completely dehydrated or lyophilized pieces (e.g., particles) of a scaffold material that has a high and reversible compressibility. This feature, together with the high porosity, allows a great flexibility in terms of adaptation to any (re-)hydration condition.

The physical, and therefore mechanical, properties of the particles comprised in the shapeable paste are at the origin of the particular properties of the paste. The particles can be dehydrated to different levels while maintaining their ability to build a cohesive paste which has a constant ability to be deformed once hydrated. To achieve this, the particles have a typical behaviour under compression: they show a "plateau pressure" over a wide range of compressive deformation (see FIG. 1). This property allows to regulate the mechanical properties of the paste on a wide range of hydration states.

In particular, the property of the paste to be shapeable can be achieved over a wide range of hydration states.

While the hydration status of the paste is comprised in the range of shapeability, the shape can be maintained, even during and after the addition or the removal of fluid from the paste, provided that the forces involved do not overcome a threshold deformation force. This results in a material that can be reversibly compressed or expanded several times while maintaining the shape it was given before.

In particular, the scaffold material of the invention can expediently be hydrated ex vivo with any material comprising a sufficient amount of water such as e.g. tissue suspensions or tissues extracts like adipose tissues (lipoaspirate) taken from a subject, or even cells, in order to create a body implant in the form of a flowable "bio-paste" that can also possibly be injected in a minimally invasive manner into the targeted tissue/organ/site to be treated (e.g. reconstructed). Additionally or alternatively, the re-hydratation can take place in situ directly after injection/placement of the scaffold material into e.g. a target tissue/organ of a subject, taking advantage of the natural water content of the injected site for the final bio-paste volume reconstitution. However, generally speaking, any kind of hand- or otherwise deformable three-dimensional objects can be obtained via hydration.

The shape of three-dimensional objects can be determined by the placement gesture/the injection procedure or the injection trajectory, the shapeable paste remaining in place and maintaining its shape and localization.

In the frame of a body volume reconstruction, the scaffold material will adapt, thanks to its intrinsic properties, to the liquid content of a second material mixed thereto, such as a tissue extract, or to the destination site it is injected in, in particular to the ratio of liquid vs cells/tissue, that can be very different among tissues or tissue extracts, while maintaining the desired mechanical properties such as shapeability. The scaffold material can further be tuned to permit, once (re-)hydrated, to match the Young's modulus of a target site, such as a body part, it is injected in, independently of additional factors.

Moreover, it is possible to achieve the setting of the scaffold paste, a certain time after implantation. As a result, the scaffold paste, if used as a body implant and injected or otherwise placed into a subject's tissue/organ, remains in a shapeable form only for a certain amount of time after injection or placement into the target site. During this period of time, the injected paste can be shaped and modelled according to the driving needs, but then a setting process "fixes" the shape of the implant, creating a stable, persistent and biocompatible volume implant which is elastic in nature.

To achieve the setting of the paste, one can for instance chose a particles' pore size and pores interconnectivity such as to allow tissue ingrowth, achieving the fixing of the paste by invasion of host tissues. Alternatively, or additionally, the scaffold particles can for instance be expediently coated with biomolecules. The setting results can be modulated for example by the type of coating performed, and/or by the activation of the in situ colonization of the scaffold by endogenous tissues and cells. Another possibility is to achieve the crosslink of particles of the scaffold by using an externally added biomolecule or reactive chemical.

Further, by injection or placement of a shapeable paste with a hydration level below the maximal hydration level, one can perform in-vivo shaping, followed by volume gain by absorption of liquid from the surrounding tissue, finally followed by paste setting.

A further aim of the present invention is to provide a medical device comprising a chamber or capsule pre-filled with the above described porous 3D scaffold material. The capsule can be e.g. plugged or pluggable to existing injecting means like syringes or needles used clinically, and is adapted to receive/accommodate a second water-containing material, such as a tissue extract, to form a mixture, said mixture being then minimally invasively injected in the form of a bio-paste into a subject's target tissue/organ through said injecting means.

Furthermore, a method for minimally invasively reconstructing a tissue/organ volume by using the porous 3D scaffold material of the invention, as well as a device as previously described, forms also part of the present disclosure.

Accordingly, it is an object of the present invention to provide for a scaffold material for use in the manufacturing of shapeable three-dimensional objects, characterized in that it substantially consists of a plurality of reversibly compressible particles of a gel-like material, said particles having a plurality of interconnected pores in their core and on their surface in connection with the external environment, said scaffold material being a shapeable paste, or becoming a shapeable paste when contacted with a liquid.

In one embodiment, the particles display upon hydration a non-linear compression behaviour with a plateau region localized in compressions ranges that are comprised between 5% and 95% compared to the fully hydrated state.

In one embodiment, the particles display upon hydration a non-linear compression behaviour with a plateau region having a minimal slope of at least 1.1 times inferior to the maximal slope observed prior to the plateau.

In one embodiment, the non-linear elastic compression behaviour of the plateau region is obtained with a hydration of the particles given by a w/w ratio between a liquid and the particles comprised between 1000 and 1, preferably between 100 and 10.

In one embodiment, the reversible compressibility volume ratio between hydrated and dehydrated state of the shapeable paste is comprised between 1.2 and 50, preferably between 2 to 15.

In one embodiment, the reversible compressibility volume ratio between fully hydrated and dry state of the shapeable paste is comprised between 2 and 1000.

In one embodiment, the particles have a mean size comprised between 1 µm and 10 cm, preferably between 10 µm and 10 mm, more preferably between 50 µm and 2 mm.

In one embodiment, the particles have a mean pore size comprised between 1 µm and 10 cm, preferably between 1 µm and 5 mm, more preferably between 1 µm and 2 mm, even more preferably between 5 µm and 500 µm.

In one embodiment, the particles have a pore diameter/pore's walls thickness ratio of at least 3, preferably above 5, preferably above 10.

In one embodiment, the overall mass of dry material content of the shapeable paste is comprised between 0.1% and 10%, preferably between 0.5% and 3%.

In one embodiment, the shapeable paste is flowable and injectable through a narrow tubular element such as a cannula or a needle.

In one embodiment, the paste is shapeable within a range of hydration states spanning from about 1% to 95% liquid volume/maximum particle volume, preferably from about 20% to 95% liquid volume/maximum particle volume.

In one embodiment, the scaffold material is characterized in that it further comprises a bioactive molecule.

In one embodiment, the scaffold material is characterized in that it further comprises cells or tissue suspensions.

Another object of the present invention relates to the use of the scaffold material previously described for in the manufacturing of shapeable tissue or organ body implants.

A further object of the present invention relates to a shapeable tissue or organ body implant, characterized in that it substantially consists of the hydrated form of the scaffold material previously described.

In one embodiment, the shapeable tissue or organ body implant is characterized in that the scaffold material comprised therein is hydrated through liquid absorption from a target tissue or organ upon insertion therein.

In one embodiment, the shape of the shapeable tissue or organ body implant is defined before, during or after insertion or placement into a target tissue or organ. In preferred embodiments, the shape of the shapeable tissue or organ body implant is defined internally or externally by manual forming or sculpting, by molding, by one or several injection procedures, by the volume or the cavity of the insertion site, by manipulation with internal or external tools, by 3D dispensing, by suturing/combining with surrounding tissues or other implants, or any combination of the foregoing.

In one embodiment, the shapeable tissue or organ body implant of claims is characterized in that the scaffold material comprised therein is hydrated through ex vivo liquid absorption from a liquid solution or a water-containing biological material mixed therewith.

In one embodiment, the shapeable tissue or organ body implant is characterized in that, upon insertion in a subject, it can expand in volume up to 100 times, preferably between 1 and 20 times.

In one embodiment, the expansion in volume of the shapeable tissue or organ body implant upon insertion in a subject is progressive.

In one embodiment, the shapeable tissue or organ body implant can expand in volume, upon insertion in a subject, in an isotropic fashion.

In one embodiment, the shapeable tissue or organ body implant is shapeable over a lapse of time comprised between 5 minutes and one month upon insertion in a subject, then becoming elastically compressible.

In preferred embodiments, the shapeable tissue or organ body implant, upon insertion in a subject, stays in place in the insertion area and does not migrate.

In one embodiment, the shapeable tissue or organ body implant, once no more shapeable after insertion in a subject, has a Young's modulus of the same order of magnitude of the surrounding tissue.

Still a further object of the present invention relates to a medical delivery device characterized in that it comprises at least a container filled with the scaffold material or with the shapeable tissue or organ body implant previously described.

Still a further object of the present invention relates to a method for creating or reconstructing a three-dimensional volume in a subject's body part, the method comprising the steps of:
Providing a scaffold material, a shapeable tissue or organ body implant and/or a medical device previously described; and
Inserting the scaffold material, the shapeable body implant and/or the content of the medical device into a subject's body part.

In one embodiment, the method is characterized in that the shapeable tissue or organ body implant and/or the scaffold material is mixed with a biological material before insertion into a subject's body part.

In one embodiment, the method is characterized in that the biological material is a liquid-containing biological material.

In one embodiment, the method is characterized in that the shapeable tissue or organ body implant and/or the scaffold material is inserted into a subject's body part through a narrow tubular element such as a cannula or a needle.

Another object of the present invention relates to a method for minimally invasively creating or reconstructing a three-dimensional volume in a subject's body part, the method comprising the steps of:
Providing a medical device previously described in the form of a syringe;
Aspirating a liquid-containing biological material using a narrow tubular element such as a cannula or a needle;
Mixing the biological material with the content of the medical device; and
Injecting/placing the so obtained shapeable tissue or organ body implant into a subject's body part.

In one embodiment, the method is characterized in that the biological material is aspired from the same subject.

In one embodiment, the method is characterized in that the biological material is blood and/or adipose tissue.

DETAILED DESCRIPTION OF THE INVENTION

Figure 1:
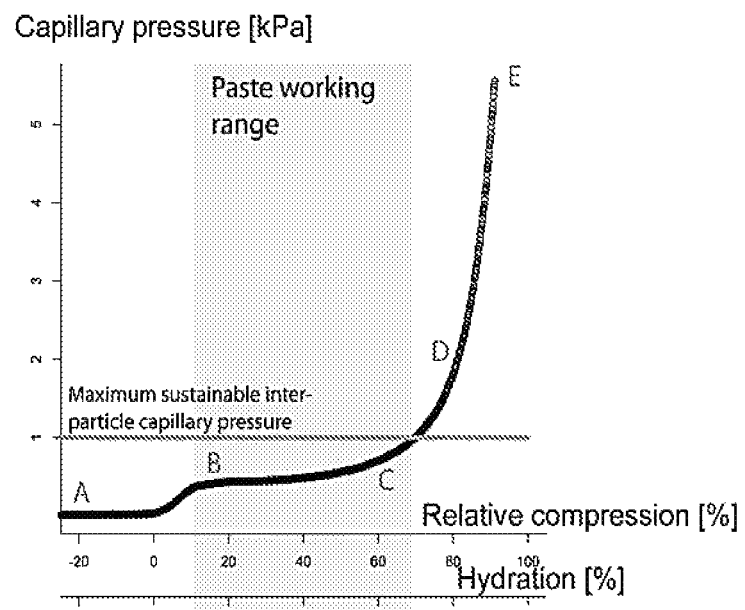
FIG. 1 shows mechanical properties of A) the material of the scaffold particles and B) the paste itself. 1A is a graph depicting the very non-linear compression response of the inter-particle capillary pressure, with a fixed plateau capillary pressure attained for a wide range of particle compression; 1B shows elastic behaviour upon forces (stress) not exceeding the shaping threshold (solid line) as compared to elastic, and then plastic behaviour when exceeding the shaping threshold (dashed line). The shaping threshold is at forces (stress) exceeding the isotropic swelling pressure, which is the pressure the paste can exert upon addition of a small amount of free liquid. In such a way, the shape can be maintained during swelling by addition of liquid.
Figure 1:
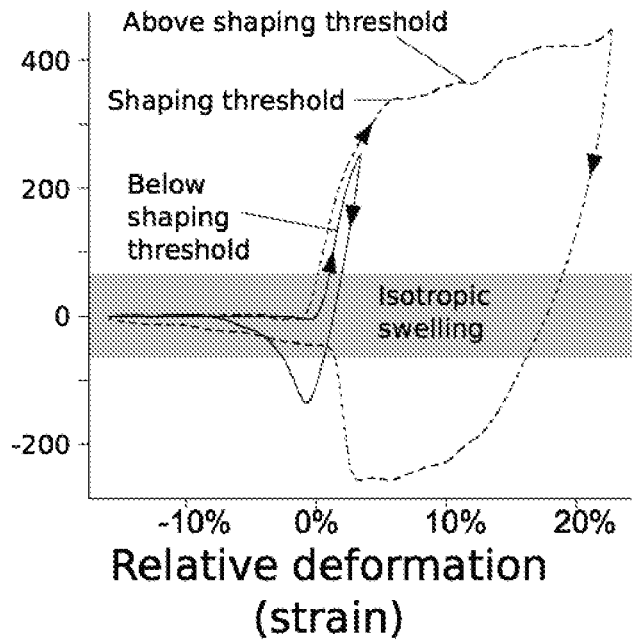

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an" and "the" include plural referents unless the context clearly dictates otherwise. Thus, for example, reference to "a particle" includes a plurality of such particles and reference to "a container" includes reference to one or more containers, and so forth.

Also, the use of "or" means "and/or" unless stated otherwise. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

The invention will be better understood with the help of the following definitions. In the frame of the present disclosure, a "scaffold material" is any three dimensional material having a framework architecture, i.e. a support structure comprising hollow spaces within it. In some embodiments, a scaffold material is an artificial structure capable of supporting three-dimensional body tissue/organ formation in vivo or ex vivo. In this context, a scaffold material is also referred herewith as a "biomaterial" or "bioscaffold". A bioscaffold may allow cell attachment and migration and/or tissue ingrowth and reorganization, may deliver and may retain cells and biochemical factors, enables diffusion of vital cell nutrients and expressed products, exerts certain mechanical and biological influences to modify the behaviour of the cell phase and so forth.

The scaffold material of the present invention is substantially composed of a plurality of particles. Said particles are highly porous, with pores interconnected among themselves and connected to the external environment and are reversibly compressible and expandable. The non-pore space of the porous particles is referred to as "wall material" or "pore lining material".

In a preferred embodiment, the particles exhibit a non-linear elastic behaviour. When the particles comes into contact with a liquid, such as a hydrating liquid, the plurality of particles can form a paste. In the frame of the present disclosure, a "paste" is a substance that behaves as a highly viscous liquid when a sufficiently large load or stress is applied.

The hydration status or hydration level is given by the relative amount of liquid in the paste. It can be expressed in terms of mass of liquid per mass of dry particle material, but more interestingly also as percentage of full hydration. Full hydration is defined herein as the minimum amount of liquid required to obtain a free particle suspension.

A material is considered shapeable if it can be deformed to arbitrary shapes by applying a force higher than a given threshold force, the achieved shapes then remaining stable against forces smaller than the threshold. In other words, the shapeable material behaves approximately as a viscous liquid for forces larger than the threshold force and as an elastic solid for forces below the threshold force. It can be repeatedly deformable by e.g. hand manipulation without fracture, or by placement by injection or with any other tool able to apply a deformation in response to applied forces such as compression, tension and the like.

As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels).

Although the shapeable paste described herein is not properly speaking a gel, it can also contain a high amount of liquid, yet have a firm consistency due to the presence of the particles. In this sense, it can be referred to as a "gel-like" material.

The wall material of the porous particles is preferably, but not exclusively, substantially made of a polymeric material suitable for creating a soft, porous structure. The particles have a mean size comprised between 1 μm and 10 cm, preferably between 10 μm and 10 mm, more preferably between 50 μm and 2 mm. As said, the particles comprised within the scaffold material are highly porous. In a preferred embodiment of the invention, the pores are interconnected among themselves in order to create a continuous net of material, and at the same time with the external environment. In some embodiments, it acts as a plausible physical support for additional elements to be put into the scaffold, while providing at the same time additional key features to the scaffold such as its softness, high compressibility, outstanding ability to regulate the capillary pressure to a target level over a wide range of hydration states and easiness of cell/tissue invasion if used in a medical context, just to cite some.

The scaffold material particles can be delivered and stored at any hydration level, including completely hydrated or dehydrated (lyophilized). They show the ability to adapt their own swelling state to the amount of water available, thus becoming a shapeable paste upon contact with a wide amount of fluid added.

In preferred embodiments, the pore size of the scaffold's particles is comprised between 1 μm and 10 cm, preferably between 1 μm and 5 mm, more preferably between 1 μm and 2 mm, even more preferably between 5 μm and 500 μm. This range of porosity is particularly convenient when the scaffold material is intended to be used as a tissue/organ implant, as will be described below in more details, since it is e.g. high enough to enable the growth of vasculature elements, connective tissues, and the like, through the porous material. As it will be evident for a person skilled in the art, the pores' size of the scaffold material particles cannot exceed the size of the particle itself. Therefore, in the frame of the present disclosure, when a particle size is referred to, it is tacitly understood that the pores thereof cannot be bigger in size. However, a pore can have a volume which is very close to that of the particle that contains it, implying that a single particle can even comprise a single pore almost filling its entire volume. In other terms, in some embodiments a single particle can be even seen as void space surrounded by a thin polymer wall.

As used herein, a "polymeric material" is any material comprising polymers, large molecules (also known as macromolecules) composed of many repeated smaller units, or subunits, called monomers, tightly bonded together by covalent bonds.

Polymer architecture at the molecular scale can be rather diverse. A linear polymer consists of a long linear chain of monomers. A branched polymer comprises a long backbone chain with several short side-chain branches covalently attached. Cross-linked polymers have monomers of one long or short chain covalently bonded with monomers of another short or long chain. Cross-linking results in a three-dimensional molecular network; the whole polymer is a giant macromolecule.

Another useful classification of polymers is based on the chemical type of the monomers: homopolymers consist of monomers of the same type, copolymers have different repeating units. Furthermore, depending on the arrangement of the types of monomers in the polymer chain, there are the following classification: the different repeating units are distributed randomly (random copolymer) or there are alternating sequences of the different monomers (alternating copolymers) in block copolymers long sequences of one monomer type are followed by long sequences of another type; and graft copolymers consist of a chain made from one type of monomer with branches of another type. Elastomers (also called rubbers) are lightly cross-linked networks while thermosets are densely cross-linked networks. Rubbers are characterised by the property of high elasticity, i.e. elastic behaviour at high stresses and strains. Polymers can be diluted in a variety of solvents (usually organic but there are a few polymers called polyelectrolytes which are water soluble). A sufficiently dense polymer solution can be cross-linked to form a polymer gel, including a hydrogel or a cryogel, which is a soft solid. Polymer materials may also be formed by blending two or more polymers into physical mixtures.

In a preferred embodiment, the wall material is a hydrogel. As used herein, the term "hydrogel" refers to a gel in which the swelling agent is water. A hydrogel is a macromolecular polymer gel constructed of a network of cross-linked polymer chains. It is synthesized from hydrophilic monomers, sometimes found as a colloidal gel in which water is the dispersion medium. Hydrogels are highly absorbent (they can contain over 90% water) natural or synthetic polymeric networks. As a result of their characteristics, hydrogels develop typical firm yet elastic mechanical properties. Hydrogels have been used in biomedical applications, such as contact lenses and wound dressings. Among the advantages of hydrogels is that they are more biocompatible than hydrophobic elastomers and metals. This biocompatibility is largely due to the unique characteristics of hydrogels in that they are soft and contain water like the surrounding tissues and have relatively low frictional coefficients with respect to the surrounding tissues. Furthermore, hydrogels permit diffusion of aqueous compositions, and the solutes, there through, and have a high permeability to water and water-soluble substances, such as nutrients, metabolites and the like.

In the embodiments where the wall material substantially consists of a hydrogel, the mechanical properties of the wall material can be tailored according to the application site by changing the hydrogel (molecular chain length, crosslinking, water content) and/or its composition. Some examples of hydrogels include, but are not limited to, natural polymers, such as polysaccharides (cellulose, modified cellulose, agarose, alginate, starch, modified starch, chitosan and many others), co-polymers of polysaccharides, polypeptides (silk, collagen, gelatin and many others), amelogenin or synthetic polymers such as silicones, polyurethanes, poly-olefins, acrylates, polyesters, polyamides, polyimides and many others.

In any case, the base material is not limiting as long as the other essential mechanical requirements (particle size, pore size, pore interconnection and so forth) are met.

The wall material may also comprise either at least one glycosaminoglycane or at least one proteoglycane, or a mixture of those two substances. The glycosaminoglycane may be for example a hyaluronic acid, chondroitinsulfate, dermatansulfate, heparansulfate, heparine or keratansulfate.

In one embodiment of the invention, the wall material comprises or consists of hyaluronic acid. The hyaluronic acid consists of glucuronic acid and acetylglucosamine which create the disaccharide hyaluronic acid. The hyaluronic acid has a fibrous, non-branched molecular structure and therefore results in highly viscous liquid solutions. Hyaluronic acid's properties can be significantly improved with crosslinking, producing a hydrogel. This added feature allows to form a desired shape, as well as to deliver therapeutic molecules, into a host. Hyaluronic acid can be crosslinked by attaching thiols, methacrylates, hexadecylamides or and tyramine. Hyaluronan can also be crosslinked directly with formaldehyde or with divinylsulfone. The hydrogel may also comprise hyaluronic acid in the form of sodium hyaluronate.

The scaffold material particles of the invention can be manufactured through any suitable manufacturing method known in the art allowing to create a highly interconnected net of pores in the material, such as e.g. (photo)lithography, 3D printing, inkjet printing, porogen leaching, emulsion freezing/freeze drying technique, inverse opal hydrogelation, cryogelation, electrospinning or fiber extrusion and bonding, gas foaming and so forth.

In a preferred embodiment, the scaffold material particles of the invention can be sterilized by at least one standard and recognized method. Some methods include autoclave, steam sterilization, gamma irradiation, ethylene oxide, UV light, among others.

In a preferred embodiment, the scaffold material particles of the invention are biocompatible, both in vitro and in vivo.

During or after the manufacturing process, the scaffold material can be functionalized with additional elements such as for instance bioactive molecules. Said elements can be coated on or embedded within the porous particles or the shapeable paste with any suitable means known in the art, and can provide additional functional properties to the material such as enhanced/reduced biodegradation, physical stabilization, biological activity and the like. In some embodiments, a bioactive molecule is added to the scaffold material or to the shapeable paste, i.e. an active agent having an effect upon a living organism, tissue, or cell. The expression is used herein to refer to any compound or entity that alters, inhibits, activates, or otherwise affects biological or chemical events.

Exemplary bioactive molecules include, but are not limited to, a protein such as a growth factor, an enzyme, an antibody or any derivative thereof (such as e.g. multivalent antibodies, multispecific antibodies, scFvs, bivalent or trivalent scFvs, triabodies, minibodies, nanobodies, diabodies etc.), a transmembrane receptor, a protein receptor, a serum protein, an adhesion molecule, a neurotransmitter, a morphogenetic protein, a matrix protein; a peptide, a polypeptide, an antigen, a nucleic acid sequence (e.g., DNA or RNA), a hormone, a cytokine, a polysaccharide, a lipid molecule, a differentiation factor, a cell and any functional fragment of the above, as well as any combinations of the foregoing. A "functional fragment" is any portion of a bioactive molecule able to exert at least one biological/physiological activity. For example, a functional fragment of an antibody could be an Fc portion, an Fv portion, a Fab/F(ab')/F(ab')$_2$ portion and so forth.

The behaviour of the partially hydrated form over a wide range of hydration status of the scaffold of the invention provides an important advantage over known scaffold materials. It allows to create tailored three dimensional objects in a quick and reliable way by simply hydrating the material without constraint in terms of available liquid (e.g., water) content.

One of the advantageous features of the porous scaffold particles described herein is a nonlinear compression behaviour including a plateau region. As used herein, the term "plateau" in a stress-strain, force-strain, or force-distance diagram of compression, designates a region with a slope inferior to the maximum slope observed so far during progressively increasing compression. In the above-mentioned diagrams, such a plateau region will appear less steep than adjacent regions, albeit not necessarily horizontal. An exemplary such diagram is depicted in FIG. 1, representing the typical behaviour of an implemented embodiment of the scaffold material of the invention upon different hydration states vis-à-vis applied compression forces. In some preferred embodiments, said plateau region is localized in compressions ranges corresponding to a hydration states comprised between 5% and 95% compared to the fully hydrated state.

In one embodiment, the particles display upon hydration a non-linear compression behaviour with a plateau region having a minimal slope of at least 1.1 times inferior to the maximal slope observed prior to the plateau. With reference to FIG. 1, upon dehydration of the particles the graph rises in terms of interparticle capillary pressure (part "A" of the graph) up to the above-referenced maximal slope (end of the "A" part). At a certain hydration level, said slope drastically flatten into the plateau region (part "B" of the graph), representing the paste working range. This behaviour represents the core inventive concept of the invented material.

The scaffold particles automatically regulate the capillary pressure in the paste to a constant level, over a wide range of hydration. More precisely, the particles have very non-linear compression response, with a capillary pressure plateau that is attained for a wide range of compression. The functional result of these properties is a large "paste working range", in which the capillary pressure is maintained below, but near the limit of maximum sustainable inter-particle capillary pressure (e.g., the capillary pressure is between 10-95% of the maximum pressure, and within the plateau range for constant mechanical properties of the paste). In this range, the paste results easily deformable, but does not break under manipulation. As shown in the exemplary embodiment of FIG. 1, for particles with a diameter comprised between 0.1 and 0.3 mm, the presence of a wide "paste working range" of at least 10%, but preferably of 50% or more of the hydration spectrum allows to obtain said malleable/shapeable paste even if mixed with materials of variable liquid content, which may not be known in advance. Generally speaking, in preferred embodiments of the invention the non-linear elastic compression behaviour present at the plateau region is obtained with a hydration of the particles given by a w/w ratio between a (hydrating) liquid and the particles comprised between 1000 and 1, preferably between 100 and 10.

In particular, it is well-known in the art that a plateau in the compression behaviour is made possible by a low solid fraction of the material used compared to the mass of a final paste, in any case below 10%, and more typically in the range of a 0.1% to a few percent in the expanded (i.e. hydrated) state. The particles used to make the shapeable paste of the invention must meet this requirement. In this context, the inventors have been able to define that the optimal overall mass of dry material content of the malleable (hydrated) paste should be comprised between 0.1% and 10% w/w, but preferably between about 0.5% and about 3%.

Figure 5:
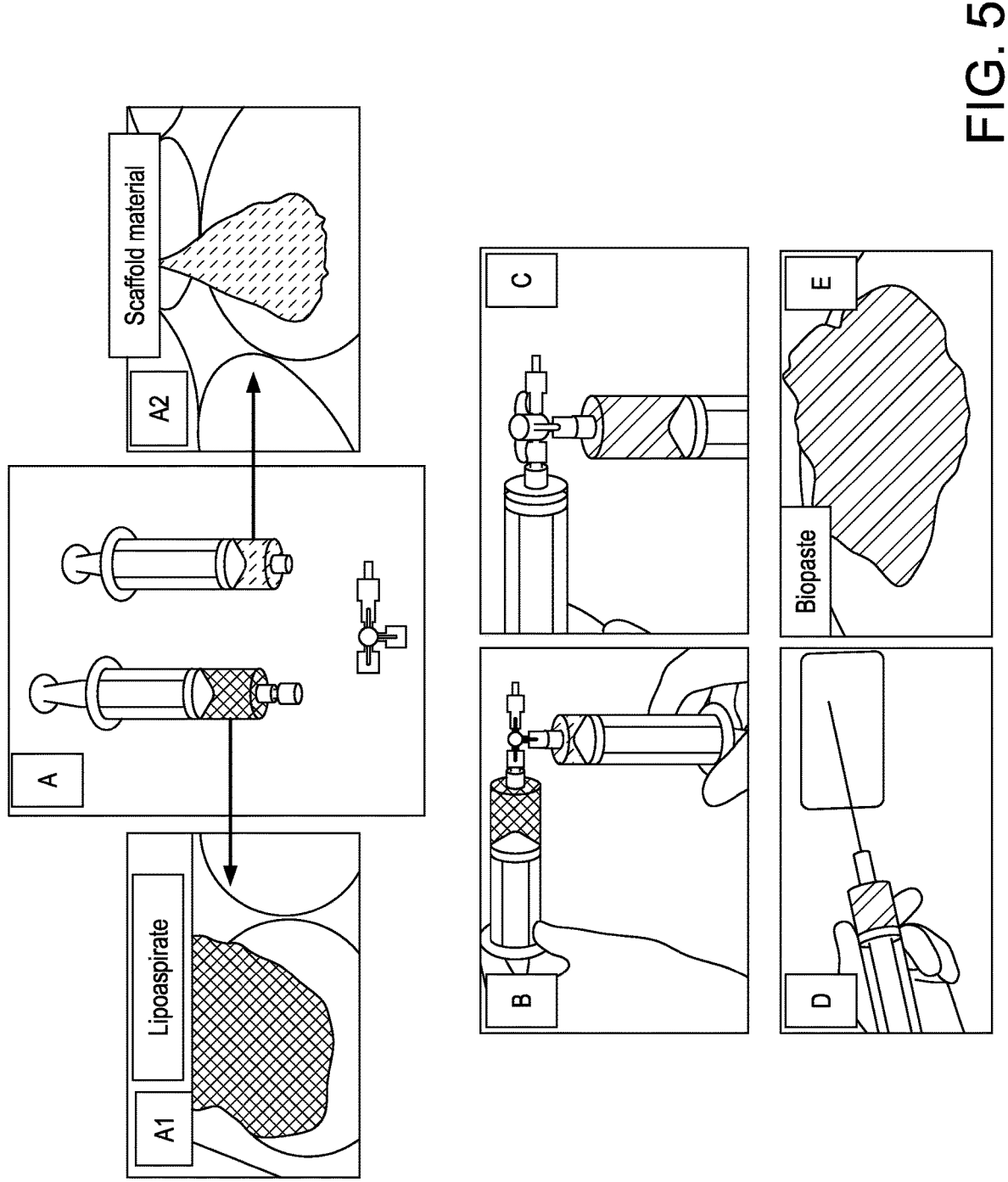
FIG. 5 shows an exemplary method of creating a malleable breast implant in the context of lipofilling.

The key features of the porous particles allowing the existence of the said plateau are that (i) the polymer walls defining the edge of the pores of the particles are thin compared to the pores themselves (the pores volume/walls thickness ratio is at least 10, preferably above 20) (ii) the pores of the particles are interconnected (interconnection is above 80%, preferably above 90%), allowing for evacuation of liquid from the pores upon compression. These parameters have been assessed as the best ones by the inventors after extensive experimental procedures, and the fabrication of a suitable polymeric material as the one shown in FIG. 5.

Figure 2:
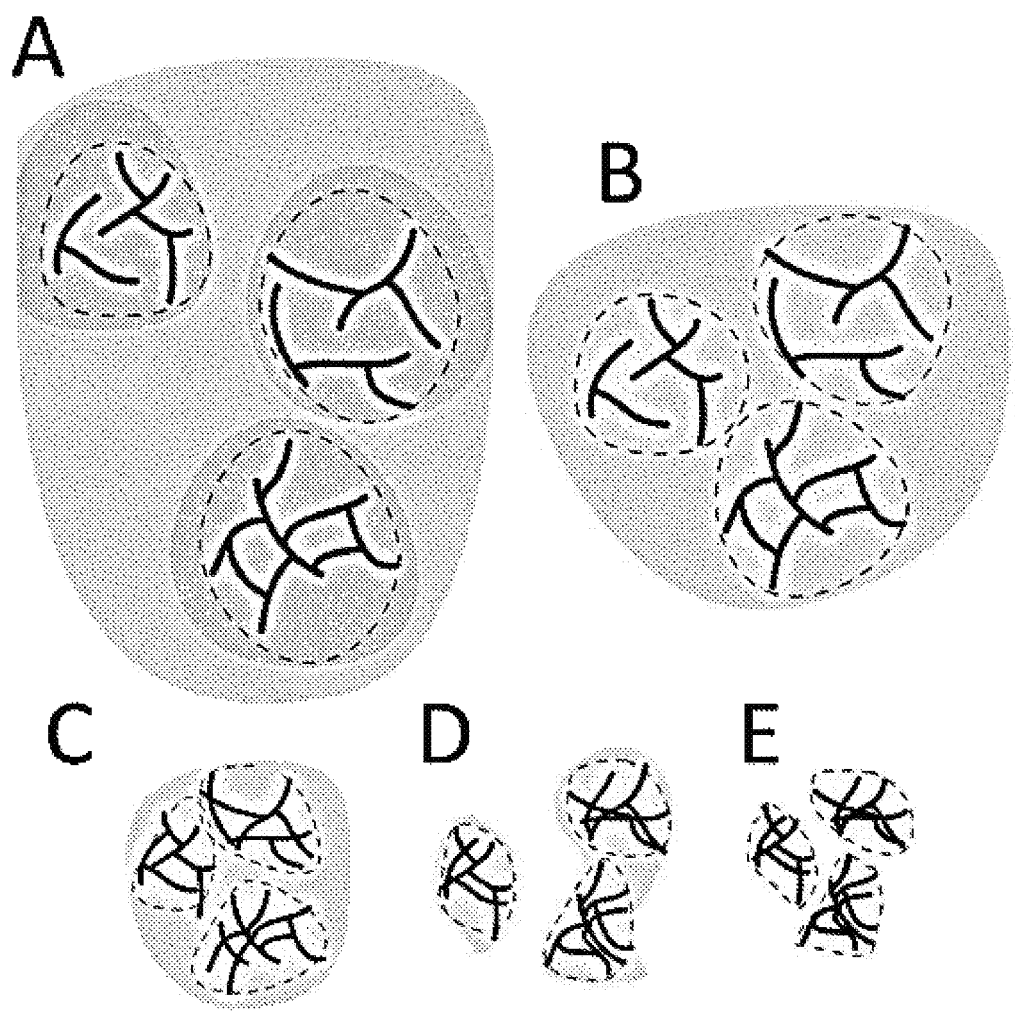
FIG. 2 shows the internal state of the paste at different levels of hydration.
Figure 3:
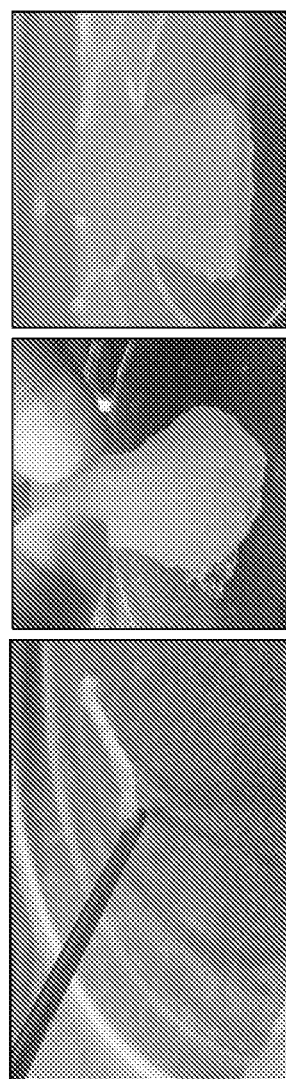
FIG. 3 shows macroscopic pictures of the shapeable paste of the invention.

FIG. 2 illustrates the internal state of the paste at different levels of hydration (labels correspond to FIG. 1). When the particles hydration gets above 100%, said particles form a free suspension. In this case, no paste is obtained, and the material is over-hydrated (FIG. 2A). With a high hydration level (in the illustrated case, about 90% hydration, FIG. 2B) the particles have absorbed a maximum quantity of liquid internally; nevertheless, their absorption capacity is not exceeded and the capillary pressure is maintained near the optimal level. The material forms a malleable paste with maximum volume. A lower hydration level (in the illustrated case, about 30% hydration, FIG. 2C) bring the particles to absorb a minimal quantity of liquid internally. Their swelling pressure is near the critical sustainable capillary pressure for the particle size chosen, but does not exceed it yet. At this hydration, the material forms a paste with minimal volume. With an insufficient hydration (in the illustrated case, 20% or less, FIG. 2D) the swelling pressure of the particle exceeds the maximum sustainable pressure for the liquid between the particles. The particles themselves remain hydrated, but air enters the inter-particle space, cohesion between the particles decreases and the paste becomes crumbly. In the extreme case of a dry material (FIG. 2E), as obtained for instance by lyophilisation, the material is in the form of a powder.

As just described referring to FIG. 2, there are two critical hydration levels:

1) an upper hydration level that corresponds in some embodiments to a range spanning between 80% and 95% of the volume at full hydration state corresponding to full particle expansion; and 2) a lower hydration level that corresponds to the beginning of pores full closure and damage of the particles. This depends on the fabrication process and on the particle mechanical characteristics. In some embodiments, this is typically comprised between 1% and 20% of the volume at full hydration state corresponding to full particle expansion.

The inter-particle capillary pressure range depends on the size of the particles. For example, for a particle size comprised between 10 µm and 500 µm, the capillary pressure that can be sustained goes up to 50 kPa, with higher values for smaller particles. As long as there is no entering of air inside the pores of the particles, the cohesion (inter-particle) pressure corresponds to the capillary (intra-particle) pressure.

Despite the existence of a paste working range, as illustrated in FIGS. 1 and 2, the changes in the mechanical properties of the paste with the hydration level are reversible. This means that the paste state can be changed at any point of time by addition or removal of liquid by suitable means. This implies that the scaffold material can be e.g. delivered at any hydration state, with the potential to reach any suitable "paste state" depending on conditions of use.

For instance, the material can be delivered dry (e.g. lyophilized) or poorly hydrated, to be mixed with a second material that contains a large fraction of liquid such as for instance a liquid (e.g., aqueous) solution, a tissue extract, a cell suspension or simply water. Upon mixing, the paste working range is reached, and the material acquires its malleable paste's properties. Alternatively, the scaffold material can be delivered dry or weakly hydrated, and e.g. injected as such into a subject in the frame of a medical setting. The scaffold particles will take up locally available liquid and will reach the paste working range in situ, after a given lapse of time. Any intermediate alternative of these two scenarios can be envisioned, such as for example the case of scaffold material particles in the lower hydration range hydrated by uptake of local liquid after injection in a subject, or by mixing with a second liquid-containing material such as a tissue extract or cell suspension, so to be brought to the upper hydration range state.

In the maximal hydration state of the malleable paste, the overall polymer content of the malleable paste is comprised between 0.1% and 10% in mass of dry polymer material, preferably between 0.5% and 3%. The progressive dehydration of the paste and therefore of the particles induces an increase of the dry polymer content up to 100%.

Upon mechanical dehydration, water is removed from the paste and the hydration level decreases. If the hydration remains above a critical level (corresponding to a loss of about up to 10 times the volume from the maximal hydration state, leading to a final polymer concentration comprised between 1% and 100% in mass), the dehydration remains reversible, and the paste is still malleable and able to gain back its original volume. The reversible compressibility volume ratio from hydrated to dehydrated state is comprised between 1.2 and 50, preferably between 2 to 15. The reversible compressibility volume ratio from hydrated to dry state is comprised between 2 and 1000.

The choice of the material constituting the particles and of the hydration means used for creating the paste have a certain inter-dependency. Actually, for example, if the working fluid is water-based, the material of which the particles are substantially constituted need to be hydrophilic (contact angle <90°, preferably)<40°; if otherwise the fluid is substantially made of an organic phase, the material likewise needs to have an affinity for the solvent (contact angle <90°, preferably)<40°. An "organic phase" is herein meant as a solution in which the solvent is a non-polar compound. Non-polar solvents are intended to be compounds having low dielectric constants and that are not miscible with water. Non-polar solutions can comprise for example solutions comprising oils, benzene, carbon tetrachloride, diethyl ether, xylene, toluene, isooctane, ethanol, heptanol, cyclohexane, hexadecane, n-octane and the like.

The plateau working range can be extended by providing additional cohesive forces between the particles, for instance by adhesive coating such as collagen, fibrin, silk, laminin, other extracellular proteins, polymers such as polyvinylalcohol, and other gluey materials that can be bound to the particles.

Another object of the invention is to provide for a malleable tissue or organ body implant, characterized in that it comprises or consists of the hydrated form of the scaffold material described above. As already explained above, the scaffold material comprised within the body implant can be hydrated through liquid absorption from a target tissue or organ upon insertion therein. Alternatively or additionally, the scaffold material is hydrated through ex vivo liquid absorption from a liquid solution or a water-containing biological material mixed therewith.

As used herein, a "body implant" is a prosthetic device used to change the size, form and/or texture of a subject's body part. Many kind of body implants are known, the most famous being breast implants. Breast implants are used to change the size, form, and texture of a woman's breast. In plastic surgery, breast implants are applied for post-mastectomy breast reconstruction, for correcting congenital defects and deformities of the chest wall and/or for aesthetic breast augmentation. For the correction of male breast defects and deformities, a pectoral implant is the breast prosthesis used for the reconstruction and the aesthetic repair of a man's chest wall. The body implant of the present invention is able to expand gradually after its injection in e.g. the breast environment, by gradually taking fluid from the body. In some embodiment, it would not be removed and it will constitute at the same time both a tissue expander and the body implant. The biomaterial-expander can in some embodiments contain biological materials such as a lipoaspirate (or other cells), and constitute a "biological" or "living" tissue expander. However, the malleable body implant of the invention can even be gradually hydrated after its insertion within a subject, by absorbing circulating fluids of the host body. This can be particularly advantageous for enabling a gradual skin growth needed for volume enhancement, for example in the context of a breast volume enhancement, and avoid the use of skin expanders. A clinician/surgeon could find the right technical protocol to be put in place on a case-by-case basis.

The body implant of the present invention could also be used for cosmetic or decorative purposes, such as for aesthetic surgery, wrinkles' treatment, subdermal or transdermal body modification and the like. It can be biodegradable, with a degradation rate comprised between several weeks to several years. The malleable paste of the body implant can have the additional benefit to enhance interstitial flow and transplant viability once injected into a subject. This is particularly useful, if not vital, in case of a body implant for medical purpose. In this case, in some embodiments the ratio between the Darcy friction factor of the malleable paste and the tissues in which it is injected can be preferably comprised between 2 and 100000.

One of the most interesting aspects of a body implant disclosed herein relates to its ability to remain shapeable over a certain time period. Compared to known body implants such as silicone breast implants, the malleability and especially the injectability character of the implant of the invention provide huge advantages in terms of invasiveness of implant procedure, design of the correct implant shape, physiological adaptation to the host's tissues and the like. However, the intrinsic mechanical properties of a malleable implant could become a problem over time if the final shape on the inserted prosthesis would not be clearly defined or fixed, and can even represent a serious health issue should the implant be allowed to continuously be reshaped once inside the host's body. Advantageously, the malleable implant of the invention can be modelled by an operator such as a surgeon upon insertion into a subject, but the subject's body will start at a certain point a series of physiological processes that will act in order to fix its shape. More precisely, as it normally happens with known implants such as silicone breast implants, when any type of those implant is inserted, the body physiologically reacts by forming a protective lining around it. This is referred to as a "capsule" or "tissue capsule", a membranous structure usually composed of dense collagenous connective tissue enveloping the implant, created by the immune response to the presence of foreign objects surgically installed to the human body. In the context of the present invention, actually, a host-produced tissue capsule forms de facto the outer layer of the malleable body implant so that said capsule represents the shell of the implant, which walls the entire core of the implant and impede any further non-elastic deformation. As a matter of fact, the final implant will be structurally similar to a silicon breast implant, i.e. it will comprise de facto an outer shell encasing a reversibly deformable soft core. Nonetheless, the implant of the invention will still be able to be invaded and colonized by host's cells and tissues, acting as a normal bioscaffold possibly resorbed by the host's cells themselves, it will be highly biocompatible and it will also reduce the risks associated to secondary complications such as a condition known as capsular contracture, i.e. the tendency of the e.g. silicon capsule structure to shrink the implant, possibly eventually squeezing its content outside the outer shell.

In this context, a further advantage of the scaffold of the present invention relies in the fact that it is devoid of any external encasing shell, that is, the malleable paste does not represent the filling portion of a precast elastic/polymeric capsule such as a silicon capsule. This avoids on one side the capsule contracture effect, and on the other hand allows the fine-tuning of the scaffold's shape without being bounded to the shape of a "container" and/or of any void space within this latter, and facilitates the possible hydration of the material through body liquid absorption, the cell invasion and/or the resorption/biodegradation of the material.

A further object of the invention relates to a medical device having at least one container filled with the above described malleable body implant and/or scaffold material particles.

Figure 4:
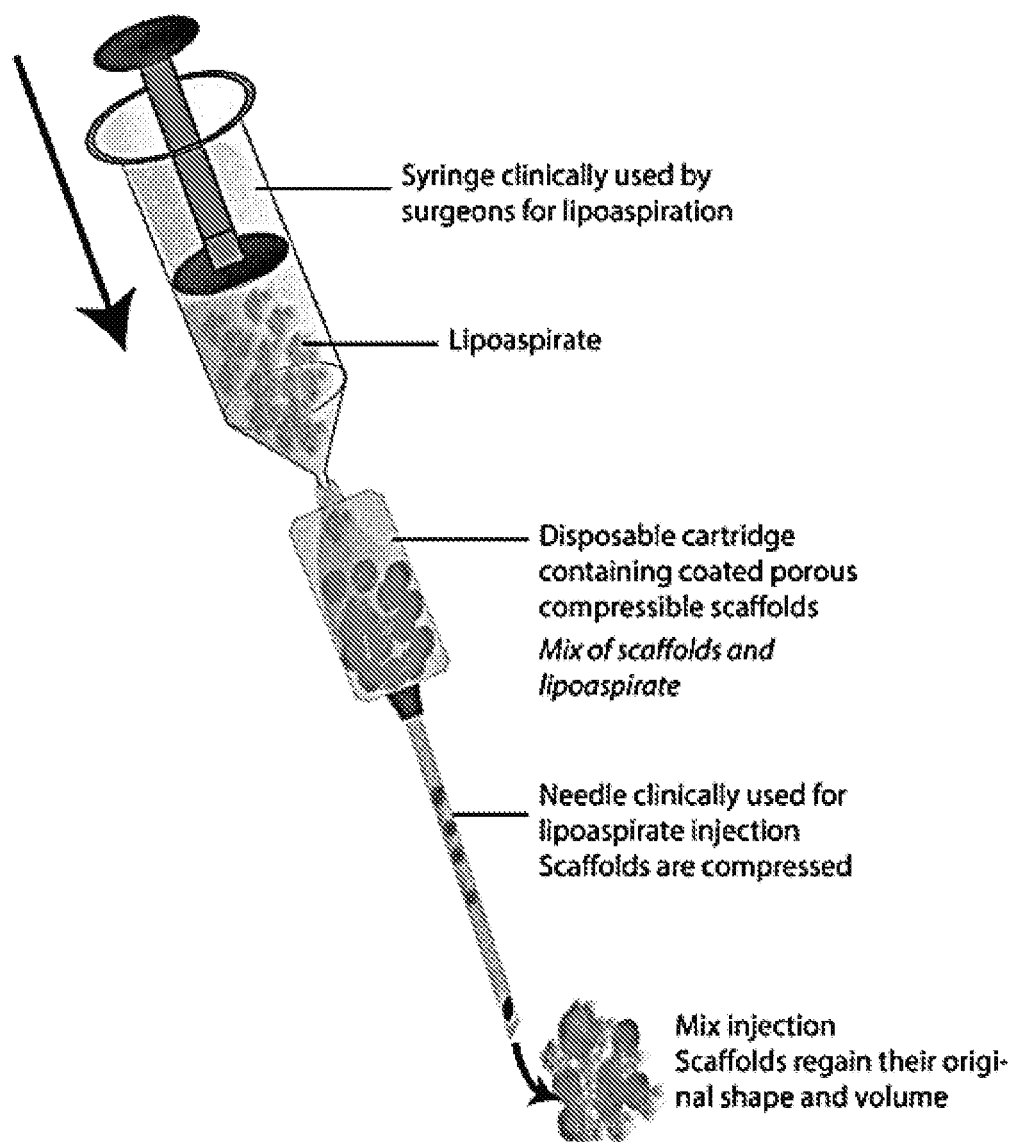
FIG. 4 shows one embodiment of the medical device of the invention.

The medical device is designed for the preparation and also preferably the application of the compressible scaffold material/malleable implant for the purpose of minimally invasive transplantation into lesions, organs or tissues to be reconstructed. In its simplest embodiment, it consists of a container such as a reservoir cartridge comprising the malleable body implant and/or scaffold material particles destined to the surgeon, for single patient use, as the one schematically depicted on FIG. 4. The disposable cartridge contains a given amount of sterile scaffold particles that are highly compressible such that mL-scale volumes can be delivered through narrow-bore tubing or needles and recover its original shape, volume and organization after the injection process. In this context, the cartridge can be operably coupled to an injection system such as one including an injection element (e.g. a needle, a catheter, a cannula) and a pressure source (e.g. a plunger). Additionally or alternatively, the cartridge can be used to mix the scaffold particles with a second liquid-containing material, for example a water-containing biological material such as a lipoaspirate, for the creation of the injectable paste (the malleable body implant) before injection. The cartridge can also be manufactured as a flexible bag (a balloon or a pocket) that can be manipulated manually or with the help of a machine. Said cartridge can also comprise more than one chamber in which all the materials are kept separated and mixed afterwards.

In a further simple embodiment, the device can be a disposable syringe that is conventionally used for lipoaspirate collection and a needle that is also clinically used for lipoaspirate aspiration and/or injection, said syringe having its reservoir filled with the scaffold material of the invention, even in a partially hydrated form. The scaffolds can be stored and delivered partially or fully dehydrated (for example by freeze-drying).

For biomedical use, the fabrication process needs to be compatible with an accepted sterilization procedure, such as autoclaving, irradiation, or gas (ethyleneoxide) treatments.

EXAMPLES

Breast lipofilling is a minimally invasive surgical technique with rapidly growing application in plastic surgery. This technique allows grafting of autologous fat tissues in liquefied form to the breast to be reconstructed. No foreign body reaction is induced, and the technique is simple to perform by the surgeon. By reinjection of the patient's own adipose tissue in a liquefied form, it reconstructs small soft tissue volumes in the most physiological way possible. However, lipofilling of larger volumes, namely after breast tumor removal, remains difficult. The grafted adipose cells starve far away from the patient's blood vessels, and the volume is lost. This is because the grafted cells do not receive enough oxygen and nutrients, and a necrotic core develops beyond about a distance of 3 mm from the nearest functional blood vessels. The technique suffers from the lack of intact vascularization in the lipo-aspirate. In large graft volumes, this leads to an imbalance between the metabolic demands of the transplanted tissue versus mass transport from the patient's vasculature. This lack of grafted cells survival is at the origin of the loose of volume observed by patients and surgeons using lipofilling for the reconstruction of intermediate and large volumes. The final results are therefore unsatisfactory for the filling of defects larger than 50 mL, concerning about 40% of all breast cancer patients.

Persistent volume lipofilling in e.g. breast cancer surgery would be of a remarkable importance for restoring bodily look and self-esteem after a devastating diagnosis. A simple, ambulatory and physiological breast reconstruction is still an unmet need in the field.

The biomaterial of the invention extends the realm of lipofilling by improving the balance between metabolic demand and mass transport:
  the metabolic demand is lowered by dilution of the lipoaspirate by the metabolically inactive biomaterial component; and
  mass transport is enhanced due to the high permeability of the porous scaffold biomaterial.

While many known hydrogel materials could be used to dilute lipo-aspirate, enhancing mass transport requires specific physical measures gathered in the biomaterial of the invention.

Two mechanisms contribute to the transport of solutes like oxygen, nutrients and waste products in living tissues: molecular diffusion, and interstitial flow. In one aspect, the fabrication process allows to obtain a material with an exceptionally high porosity, combined with large and interconnected pores. This pore structure offers little additional resistance to molecular diffusion, and provides a low-resistance pathway for interstitial flow, greatly enhancing transport by interstitial flow. The optimized ratio between demand and mass transport enables the use of the bio-paste at volumes where classical lipofilling would yield poor clinical results due to tissue necrosis. Currently, in very large reconstruction volumes, a drainage for exudate typically has to be maintained for a period postoperatively. The present biomaterial will favourably exploit the associated large interstitial flow.

A second key aspect of the biomaterial of the invention is its fine-tunable mechanical properties, which render it particularly appropriate in e.g. a lipofilling context. Mixed with a second material having a sufficient water content, such as a lipo-aspirate, it is an injectable material with consistent mechanical properties. Once injected, the material first retains paste-like properties, allowing "sculpting" by an operator (e.g. plastic surgeon). Cellular colonization then yields a solid that matches the Young modulus of the soft tissues it replaces, minimizing scarring and foreign body reaction, while providing at the same time an implant perfectly fitting the host tissue properties and studied to optimize vascular ingrowth.

A third unique key feature of the biomaterial of the invention relies in the fact that the particles are endowed with a high, yet regulated liquid absorption power. Whatever the liquid content of the second material/tissue it comes into contact is, the biomaterial is able to adapt itself to it in order to give a malleable biological paste, thus compensating for a wide range of hydration status of the e.g. lipo-aspirate material with which it is mixed. If the lipo-aspirate contains a lot of fluid, the particles swell more, while if the lipo-aspirate contains more adipocytes, the particles swell less. As a result, the cohesion force and mobility of the final paste remain constant and controlled despite widely varying technical conditions. The consistency of the final paste allows for injection through a syringe needle, yet enables sculpting of the material by the plastic surgeon. All these features provide several real life advantages for both the patients and the surgeons.

For The Patient:
  Volume stability in time, no need of additional surgery for maintaining the reconstructed volume;
  Less invasive surgery than the implantation of breast prosthesis or flap tissues insertion, uncomplicated procedure, patient is discharged from hospital on the first postoperative day;
  Reduced risk of rejection or capsular contracture compared to prosthesis implantation;
  Long-term biodegradation of the scaffold possible, allowing the replacement of the scaffold by endogeneous tissues, extracellular matrix and vascularization system. On the very long-term: completely "biological" and autologous volume reconstruction;
  Lighter volumes than in the case of silicone prosthesis, allowing to reconstruct higher volumes without side-effects related to the weight of the prosthesis.

For The Surgeon:
  No need of additional step in the conventional lipofilling protocols. The invention is construed to be directly integrated in the existing surgical protocols;
  Possibility to adapt the use of the device regarding patient needs (several sizes or volumes available, several proportion of lipoaspirate vs scaffolds can be used);
  Higher short term and long term satisfaction of the patient.

Hereinafter is described an exemplary method of using the scaffold material in the context of lipofilling:
  1) The surgeon collects the lipoaspirate (or other tissues/cells) from the patient in a syringe (FIG. 5A). In the particular case of lipoaspirate, it can be prepared by different methods before being further used (centrifugation, decantation, rinsing). This step depends on the surgeon practice. One of the advantage of the method is the possibility of using the same lipoaspirate tissues from the patient that are currently used for reconstructive surgeries.

2) When ready, the syringe containing the tissues/cells to be grafted is connected (screwed) to the cartridge containing the porous scaffold material (FIG. 5B). The particles composing the scaffold material can be specifically coated (with e.g. proteins, growth factors, molecules of the extracellular matrix or polymers), for example in order to enhance cells/tissues adherence to them, if needed. A needle is screwed at the other side of the cartridge. If needed, the cartridge is shaken or "mixed" form the outside manually or using a machine in order to mix the two components and create the scaffold "biopaste" (the paste made of scaffolds and the biological tissues).

3) The surgeon performs a small incision to insert the needle and injects the lipoaspirate (or other cells/tissues) (FIG. 5C). The lipoaspirate flows in the cartridge and hydrates (fully or partially) the porous scaffolds. A "composite" mixture is thus created. The scaffolds parts and the lipoaspirate assemble. The scaffolds being compressible, the whole preparation can be injected through the needle (FIG. 5D) without damage to the scaffolds or to the cells/tissues.

Alternatively, steps 1 to 3 above can be replaced by a single step envisaging the use of a medical device in the form of a syringe already comprising into its reservoir the scaffold material particles or the malleable implant of the invention, and the aspiration of a liquid-containing biological material such as blood or lipoaspirate from the syringe needle, possibly directly from the patient him/herself. The aspiration permits the direct mix of the reservoir's content with the biological material so that a suitable biopaste is immediately created and ready to be injected.

4) The surgeon places the device's needle inside the targeted organ/place/tissue of the patient and applies a positive pressure to the device so that the mixture flows out the needle.

5) Thanks to particular mechanical properties, once injected (for example subcutaneously) the scaffolds parts retrieve their original shape and volume. In addition, the mixture can be remodelled manually by the surgeon, allowing the perfect shaping and forming of the injected volume.

The invention claimed is:

1. A scaffold material for use in manufacturing shapeable three-dimensional body implants, wherein:
    the scaffold material consists essentially of a plurality of elastically compressible particles;
    the particles have a plurality of interconnected pores in their core and on their surface that are connected to an environment external to said particles;
    non-pore space of the particles is wall material;
    the wall material comprises a macromolecular polymer gel constructed of a network of covalently cross-linked polysaccharides and co-polymers of polysaccharides;
    the pores have a mean pore diameter between 1 μm and 2 mm;
    the particles have a ratio of mean pore diameter to wall material thickness of at least 3;
    the scaffold material is a shapeable paste, or becomes a shapeable paste when contacted with a liquid; and
    a reversible compressibility volume ratio between a hydrated state and a dehydrated state of the shapeable paste is between 1.2 and 50.

2. The scaffold material of claim 1, wherein the particles are hydrated to a w/w ratio between the liquid and the particles of between 1000 and 1.

3. The scaffold material according to claim 1, wherein the reversible compressibility volume ratio between the hydrated state and the dehydrated state of the shapeable paste is between 2 and 15.

4. The scaffold material of claim 1, wherein the shapeable paste is flowable and injectable through a narrow tubular element.

5. The scaffold material of claim 1, further comprising a bioactive molecule.

6. The scaffold material of claim 1, further comprising cells or tissue suspensions.

7. A shapeable tissue or organ body implant consisting essentially of a hydrated form of the scaffold material of claim 1.

8. The shapeable tissue or organ body implant of claim 7, wherein the scaffold material is at least partially hydrated through liquid absorption from a target tissue or organ upon insertion therein.

9. The shapeable tissue or organ body implant of claim 7, wherein the scaffold material is at least partially hydrated through ex vivo liquid absorption from a liquid solution or a water-containing biological material mixed therewith.

10. The shapeable tissue or organ body implant of claim 7, wherein a shape of the shapeable tissue or organ body implant is defined before, during or after insertion or placement into a target tissue or organ.

11. The shapeable tissue or organ body implant of claim 7, wherein a shape of the shapeable tissue or organ body implant is defined internally or externally by manual forming or sculpting, by molding, by one or several injection procedures, by a volume or a cavity of an insertion site, by manipulation with internal or external tools, by 3D dispensing, by suturing, by combining with surrounding tissues or other implants, or any combination thereof.

12. The shapeable tissue or organ body implant of claim 7, wherein upon hydration, the shapeable tissue or organ body implant is expandable in volume up to 100 times.

13. The shapeable tissue or organ body implant of claim 7, wherein upon hydration, the shapeable tissue or organ body implant is expandable in volume and the expansion in volume is progressive.

14. The shapeable tissue or organ body implant of claim 7, wherein the shapeable tissue or organ body implant is expandable in volume, upon hydration in an isotropic fashion.

15. The shapeable tissue or organ body implant of claim 7, wherein upon insertion in a subject, the shapeable tissue or organ body implant stays in place in an insertion area and does not migrate.

16. The shapeable tissue or organ body implant of claim 7, wherein once no more shapeable after insertion in a subject, the shapeable tissue or organ body implant has a Young's modulus of a same order of magnitude of surrounding tissue.

17. A medical delivery device comprising at least a container filled with the scaffold material of claim 1.

18. A scaffold material according to claim 1 configured so as to create or reconstruct a three-dimensional volume in a subject's body part.

19. A shapeable tissue or organ body implant according to claim 7 configured so as to create or reconstruct a three-dimensional volume in a subject's body part.

20. The scaffold material according to claim 1, wherein the scaffold material is mixed with a biological material.

21. The scaffold material according to claim 1, wherein the particles display, upon hydration, a non-linear compression behavior with a plateau region localized in compression ranges that are between 5% and 95% of a fully hydrated state.

22. The scaffold material according to claim 1, wherein the polysaccharides comprise modified cellulose, alginate, or hyaluronic acid.

* * * * *